United States Patent
Le et al.

(10) Patent No.: US 11,591,562 B2
(45) Date of Patent: Feb. 28, 2023

(54) MODULAR OXYGEN MONITOR

(71) Applicant: Billups-Rothenberg, Inc., San Diego, CA (US)

(72) Inventors: Royal Q. Le, San Diego, CA (US); Kyong Son, San Diego, CA (US); Barry E. Rothenberg, San Diego, CA (US)

(73) Assignee: BILLUPS-ROTHENBERG, INC., San Diego, CA (US)

( * ) Notice: Subject to any disclaimer, the term of this patent is extended or adjusted under 35 U.S.C. 154(b) by 632 days.

(21) Appl. No.: 16/719,839

(22) Filed: Dec. 18, 2019

(65) Prior Publication Data

US 2020/0190459 A1    Jun. 18, 2020

Related U.S. Application Data

(60) Provisional application No. 62/781,223, filed on Dec. 18, 2018.

(51) Int. Cl.
| | |
|---|---|
| *C12M 3/00* | (2006.01) |
| *C12M 1/34* | (2006.01) |
| *C12M 1/36* | (2006.01) |
| *C12M 1/00* | (2006.01) |

(52) U.S. Cl.
CPC .......... *C12M 41/34* (2013.01); *C12M 1/3476* (2013.01); *C12M 41/14* (2013.01); *C12M 41/40* (2013.01); *C12M 41/48* (2013.01); *C12M 1/36* (2013.01)

(58) Field of Classification Search
CPC .... C12M 41/34; C12M 1/3476; C12M 41/14; C12M 41/40; C12M 41/48; C12M 1/36
USPC ............................ 435/3, 41, 325, 243, 287.1
See application file for complete search history.

(56) References Cited

U.S. PATENT DOCUMENTS

| | | | |
|---|---|---|---|
| 2018/0066223 A1* | 3/2018 | Lim | C12M 41/48 |
| 2020/0017817 A1* | 1/2020 | Kelly-Greene | C12M 1/32 |

FOREIGN PATENT DOCUMENTS

| | | | |
|---|---|---|---|
| JP | 2016-503299 | * | 2/2016 |
| JP | 6544699 | * | 6/2019 |

* cited by examiner

*Primary Examiner* — Fred Prince
(74) *Attorney, Agent, or Firm* — Umberg Zipser LLP (57) ABSTRACT

Provided herein are systems for continuously measuring oxygen and carbon dioxide gas levels inside a cell culture incubator, comprising an oxygen sensor that uses LED based fluorescence technology to determine the amount of oxygen in the surrounding atmosphere, a carbon dioxide sensor that uses LED based Non-dispersive Infra-Red (NDIR) technology to determine the amount of carbon dioxide in the surrounding atmosphere, and electronics to wirelessly monitor the output from the oxygen sensor and carbon dioxide sensor. Most preferably, the system can be placed inside a cell culture incubator, and sensor readings are pre-compensated for temperature, pressure, and humidity. Also provided herein are methods of using the same.

15 Claims, 5 Drawing Sheets

MODULAR OXYGEN MONITOR

This application claims priority to our U.S. Provisional Patent Application with the Ser. No. 62/781,223, which was filed Dec. 18, 2018, and which is incorporated by reference herein.

FIELD OF THE INVENTION

The field of the invention relates to devices and methods for monitoring environmental parameters, and particularly continuously monitoring oxygen and carbon dioxide levels inside a cell culture incubator.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Molecular oxygen (i.e., $O_2$) is essential for aerobic respiration. While the concentration of oxygen in the atmosphere is approximately 21%, cells derived from multicellular eukaryotes, especially animal cells, are generally adapted to lower oxygen levels. Thus, it is generally desirable for in vitro cultures of such mammalian cells to expose the cells to specific amounts of oxygen in the cell culture chamber for optimal growth. In most cases, the amount of oxygen is lower than that of the atmosphere. With increasing interest in the performance of cell culture experiments under various oxygen levels, a range of technologies and instruments have been developed.

Most commonly, the concentration of oxygen within an incubator is controlled using a predefined gas mixture, or via individual gas sources (such as tanks with compressed gas) for which the volume of gas flow can be regulated to so generate a mixture with a desired oxygen content. Actual oxygen quantities in the incubator are then typically measured with oxygen sensors that are integral with the incubator. Unfortunately, such measurements are often not very accurate, particularly where strong excursions of oxygen content occur (e.g., due to opening of a door), or where the gas composition of the gas mixture temporarily fluctuates. Still further, and particularly where cells are grown under hypoxic conditions in an atmospherically controlled modular container that is placed in a larger incubator (see e.g., U.S. Pat. Nos. 9,315,769 or 10,138,455), measurement of the oxygen concentration within such modular containers is typically not known in the art.

Thus, even though various devices and methods for analyzing gas mixtures, and especially oxygen content in an incubator for cell culture are known in the art, all or almost all of them suffer from various disadvantages. Consequently, there is a need to provide improved devices and methods that allow for accurate and rapid determination of atmospheric parameters, and particularly $O_2$ and $CO_2$.

SUMMARY OF THE INVENTION

The inventive subject matter is directed to devices and methods that allow for continuous and quantitative analysis of various environmental parameters, and especially oxygen and carbon dioxide concentrations in the gas space of an atmospherically controlled cell culture container that may be disposed in an incubator. In particularly preferred aspects, contemplated devices will represent an autonomous drop-in solution that is simply placed in a cell culture container without the need for specialized wiring and/or other attachments.

In one aspect of the inventive subject matter, the inventors contemplate a method for continuously measuring oxygen and carbon dioxide concentrations inside a cell culture container. Most typically, such method will include a step of providing an environmental sensor device and placing the environmental sensor device into a cell culture container, wherein the sensor device comprises a solid state oxygen sensor and a solid state carbon dioxide sensor. In another step, a controlled hypoxic atmosphere is established within the cell culture container, placing the cell culture container is placed into an incubator. In yet another step, the environmental sensor device is used to continuously measure oxygen and carbon dioxide concentrations within the cell culture container while the cell culture container is located within the incubator. In a still further step data from the solid state oxygen sensor and the solid state carbon dioxide sensor are stored in a memory and/or wirelessly transmitted to a user while the cell culture container is located within the incubator. The data may be stored or transmitted in predetermined intervals and/or may be associated with a time stamp.

In additionally contemplated embodiments, the method may also include a step of measuring ambient pressure, humidity, and/or temperature while the cell culture container is located within the incubator, and where desired, a step of using the measured ambient pressure, humidity, and/or temperature to determine adjusted quantities for the oxygen and carbon dioxide concentrations. The adjusted quantities for the oxygen and carbon dioxide concentrations may then be displayed on a display while the cell culture container is located within the incubator.

Most typically, the controlled hypoxic atmosphere in the cell culture container is established using a gas feed into the cell culture container, while the gas feed is preferably provided from a gas source outside the incubator. Additionally, or alternatively, it is contemplated that the environmental sensor device measures the oxygen and carbon dioxide concentrations in the cell culture container by passive diffusion of oxygen and carbon dioxide through a gas permeable hydrophobic membrane that separates the solid state oxygen sensor and/or the solid state carbon dioxide sensor form the cell culture container. Moreover, it is contemplated that the user may send a wireless signal to the environmental sensor device to wirelessly transmit the data to the user.

Therefore, the inventors contemplate an environmental sensor device that includes a housing that at least partially encloses first and second solid state sensors, wherein the first solid state sensor comprises an oxygen sensor having an oxygen quenchable fluorescent dye, and wherein the second solid state sensor comprises a non-dispersive infrared (NDIR) carbon dioxide sensor. An electronic component is preferably coupled to the first and second solid state sensors and further comprises a memory for data storage and a wireless communication module that allows for transmission of data while the sensor device is located inside the cell culture incubator. Most typically, the electronic component is also configured to compensate sensed amounts of oxygen and carbon dioxide for temperature, pressure, and humidity, to so determine adjusted quantities for oxygen and carbon dioxide. In further preferred aspects, the housing is configured to form a self-contained sensor device suitable for placement inside a cell culture incubator.

As noted above, it is generally contemplated that the device further includes an ambient pressure sensor, a humidity sensor, and/or a temperature sensor, and that the electronic component is configured to use data from the ambient pressure sensor, the humidity sensor, and/or the temperature sensor to the determine the adjusted quantities for oxygen and carbon dioxide. Preferably but not necessarily, the device also has a display that is coupled to the electronic component and that is configured to display the adjusted quantities for oxygen and carbon dioxide. Additionally, it is preferred that the device includes a power source disposed within the housing, optionally coupled to a sensor that to measure charge status of the power source.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus, if one embodiment comprises measuring oxygen, carbon dioxide, temperature and pressure and a second embodiment comprises measuring oxygen and humidity, then the inventive subject matter is also considered to include other remaining combinations of oxygen, carbon dioxide, temperature, pressure, and humidity, even if not explicitly disclosed.

Figure 1:
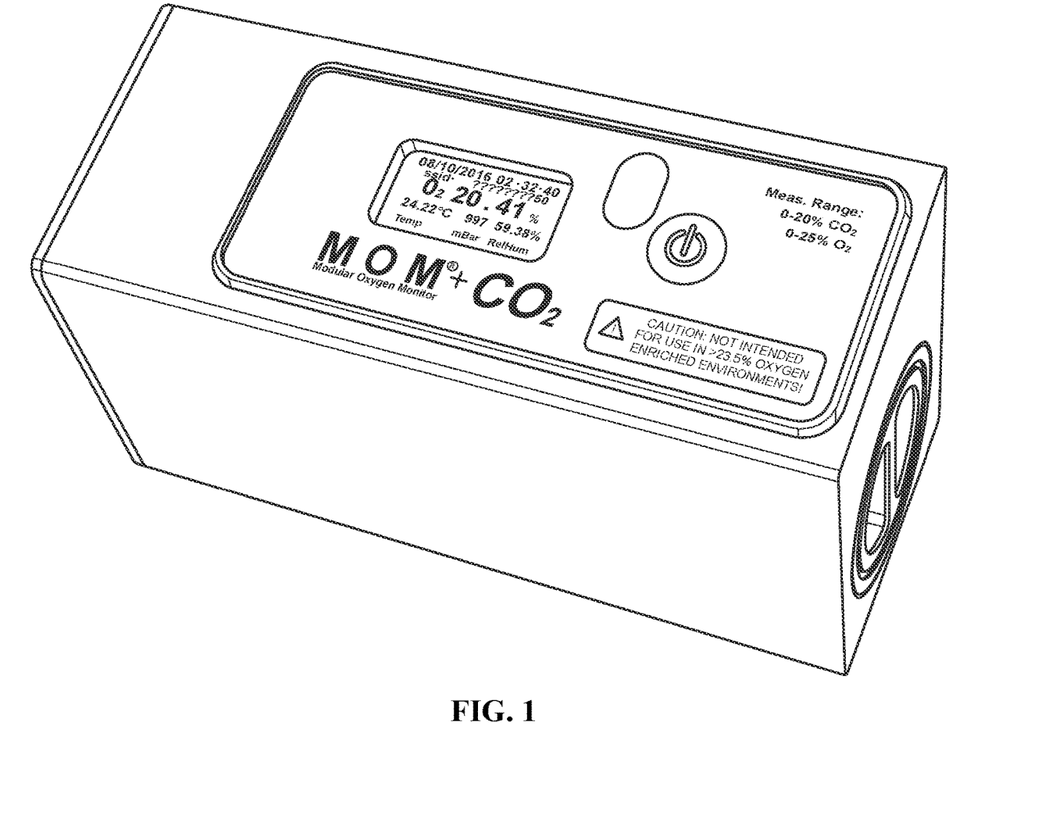
FIG. 1 is a photograph of one exemplary embodiment of the environmental sensor device disclosed herein.

As further discussed in more detail below, the inventors have developed a self-contained autonomous environmental sensor device that can be simply placed into a cell culture container and that, upon activation, continuously measures oxygen and carbon dioxide concentration in the gas space of the cell culture container. The so measured quantities can then be displayed on the device and/or wirelessly transferred to a user device (e.g., mobile phone, tablet, router, desktop computer, etc.) while the environmental sensor device is in the cell culture container (which in turn may be disposed in an incubator), and FIG. 1 shows an exemplary embodiment of a sensor device contemplated herein.

Most mammalian cell cultures require oxygen levels that are less than the atmospheric level of approximately 21 vol %. Indeed, as has become more recently apparent, many cell and tissue types are highly sensitive to a change in oxygen in the cell culture container, and will exhibit significant changes in gene expression, metabolic pathway usage, etc. even with relatively minor changes in oxygen content in the cell culture container. As such, it has become increasingly important to accurately measure and record oxygen concentrations throughout the duration of the cell culture.

Notably, the systems and methods contemplated herein have several advantages over currently known technologies, including compact size, rapid and real-time measurement of various environmental parameters including oxygen and carbon dioxide concentration, barometric pressure, temperature, and/or humidity, all of which contribute to high accuracy while enabling a form factor that allows placement of the sensor in the cell culture container during continuous operation. Moreover, where the sensors measure barometric pressure and temperature, test results can be normalized to any geographic location (e.g., compensation for higher altitude) and/or other variables (e.g., high- or low temperature growth conditions). Thus, and viewed from a different perspective, contemplated devices are self-calibrating. In addition, it should be noted that all data can be stored (typically in association with a time stamp) and/or wirelessly transmitted to a remote device, which allows continuous monitoring in situ without disturbance while the cell or tissue culture is in the cell culture container. Of course, it is also noted that the devices contemplated herein may communicate with external systems to store data, and that multiple devices can be simultaneously monitored. Furthermore, because the system is placed inside the cell culture incubator, continuous and instant monitoring of the conditions inside the incubator is possible.

The sensors in preferred embodiments are solid state sensors and are pre-calibrated. Such sensors generally benefit from low-power operation, typically associated with electrochemical sensors, while providing a much longer lifetime due to the non-depleting sensing principle. As noted above, oxygen sensors are preferably pressure and temperature compensated, enabling accurate operation over a wide environmental range without the need for additional calibration. As is known to a skilled artisan in the art, the amount of a gas is related to the pressure and temperature by the ideal gas law, which is often written as $PV=nRT$, where P, V and T are pressure, volume, and temperature, n is the number of moles of gas, and R is the ideal gas constant. Thus, it should be appreciated that a change in temperature, pressure, and/or volume inside the incubator may lead to a change in amount of a gas, such as oxygen. Unfortunately, most if not all currently known systems fail to even recognize excursions as being critical to experimental outcomes. As such, many experimental results cannot be compared due to the differences in oxygen, which leads to significant changes in gene expression and metabolism.

Thus, the devices disclosed herein accommodate for changes in pressure and temperature and will accurately read the amount of oxygen and carbon dioxide present in the cell culture container. Furthermore, unlike other oxygen sensor technologies available in the market, the instant system of sensors for oxygen sensing devices are stable and do not contain lead or any other hazardous materials.

In particularly preferred aspects, the system disclosed herein comprises an oxygen sensor that uses LED based fluorescence technology to determine the amount of oxygen. Here, the oxygen sensor comprises an oxygen quenchable fluorescent dye, which means that the dye will give up some of its absorbed energy to the oxygen molecules in the environment rather than release the energy as fluorescence. Thus, as the concentration of oxygen increases, the fluorescence emission proportionally decreases, and the amount of oxygen can be measured.

Likewise, the system disclosed herein further comprises a carbon dioxide sensor that uses LED based non-dispersive infrared (NDIR) technology to determine the amount of carbon dioxide. For measuring the amount of carbon dioxide, an IR source emits a beam of IR light containing a wide energy spectrum. When a sample of gas is pumped into the gas sample chamber, certain gases such as carbon dioxide, act as a filter absorbing a specific wavelength of energy within the IR spectrum. Other gases in the sample will not absorb that wavelength of IR light. In an NDIR sensor measuring carbon dioxide, a wavelength filter placed just before the IR detector only allows that wavelength of IR energy absorbed by carbon dioxide to pass through. The IR detector measures the concentration of that wavelength of IR light after it has passed through the sample. Thus, there is an inverse relationship between the amount of carbon dioxide in the gas sample and the amount of IR light detected at the target energy level. When there is no carbon dioxide in the chamber, all of the IR light will reach the detector. Therefore, the greater the concentration of carbon dioxide in the gas sample, the greater the IR light absorbed at that energy and the less IR light that is detected by the IR detector. Using this energy measurement, the sensor calculates the concentration of carbon dioxide in the gas sample.

It should further be noted that use of such solid state sensors will minimize heating of the surrounding environment compared to other currently known technologies for measuring carbon dioxide, and thus helps in maintaining a steady temperature within the cell culture incubator. Such is particularly relevant when the sensor device is disposed within a relatively small and/or modular container that is placed in a larger incubator.

Figure 2:
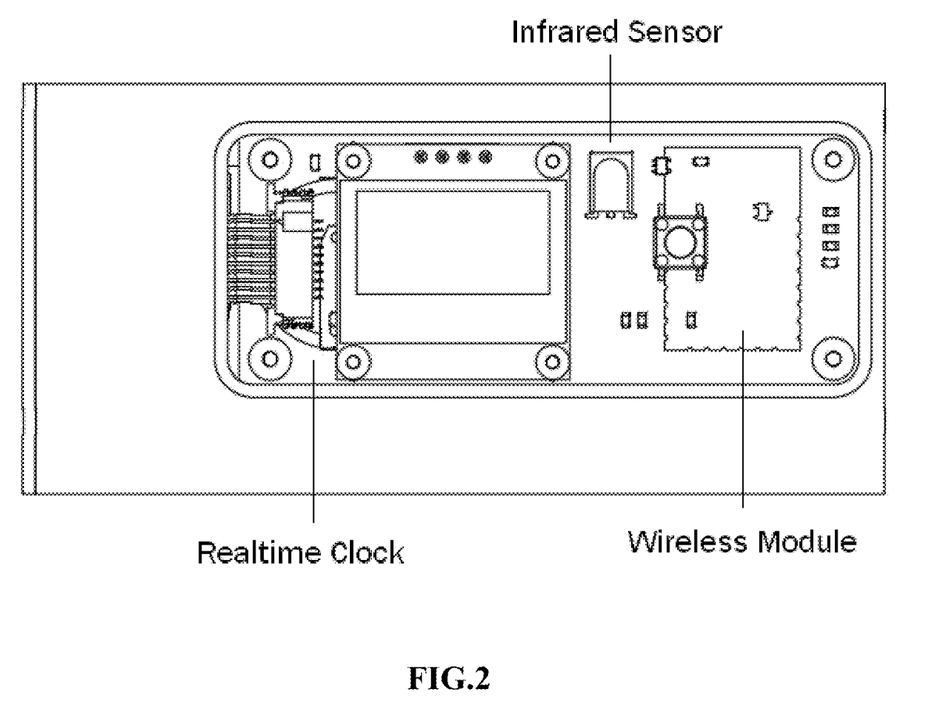
FIG. 2 is a schematic illustration of exemplary components and placement thereof for the device of FIG. 1.
Figure 3:
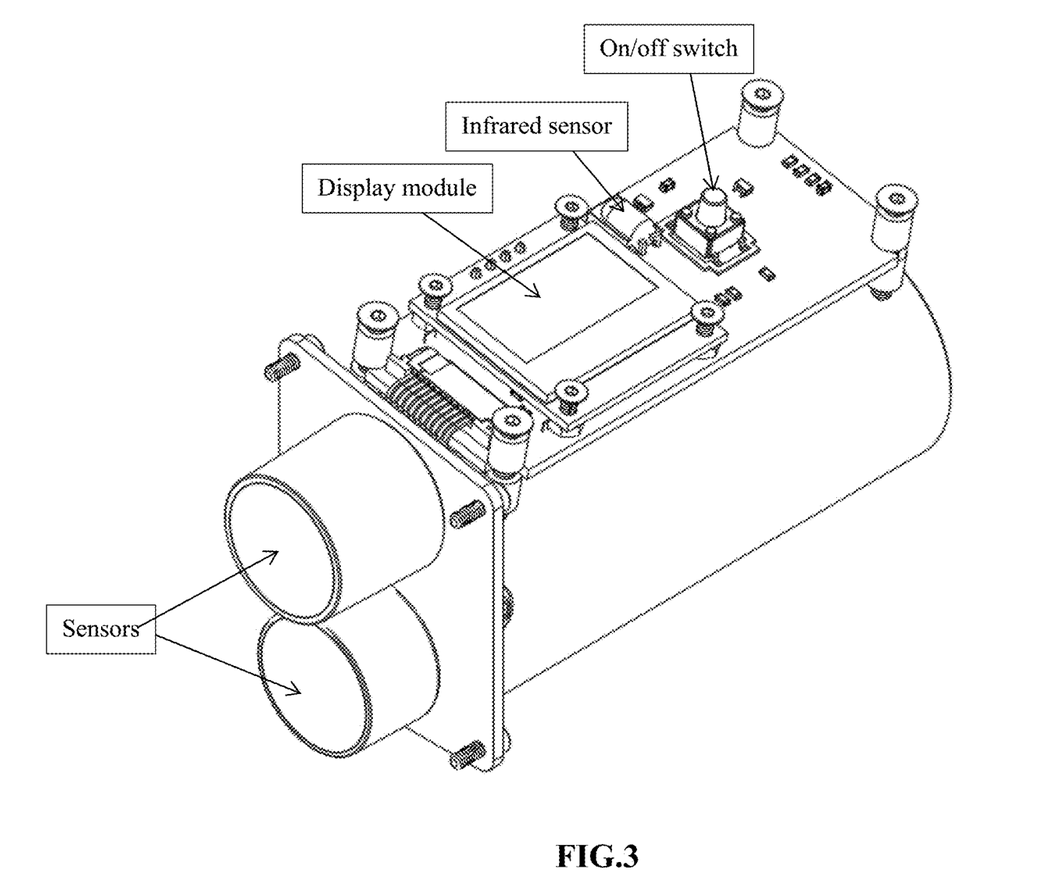
FIG. 3 is a schematic detail view of exemplary components and placement thereof for the device of FIG. 1.
Figure 4:
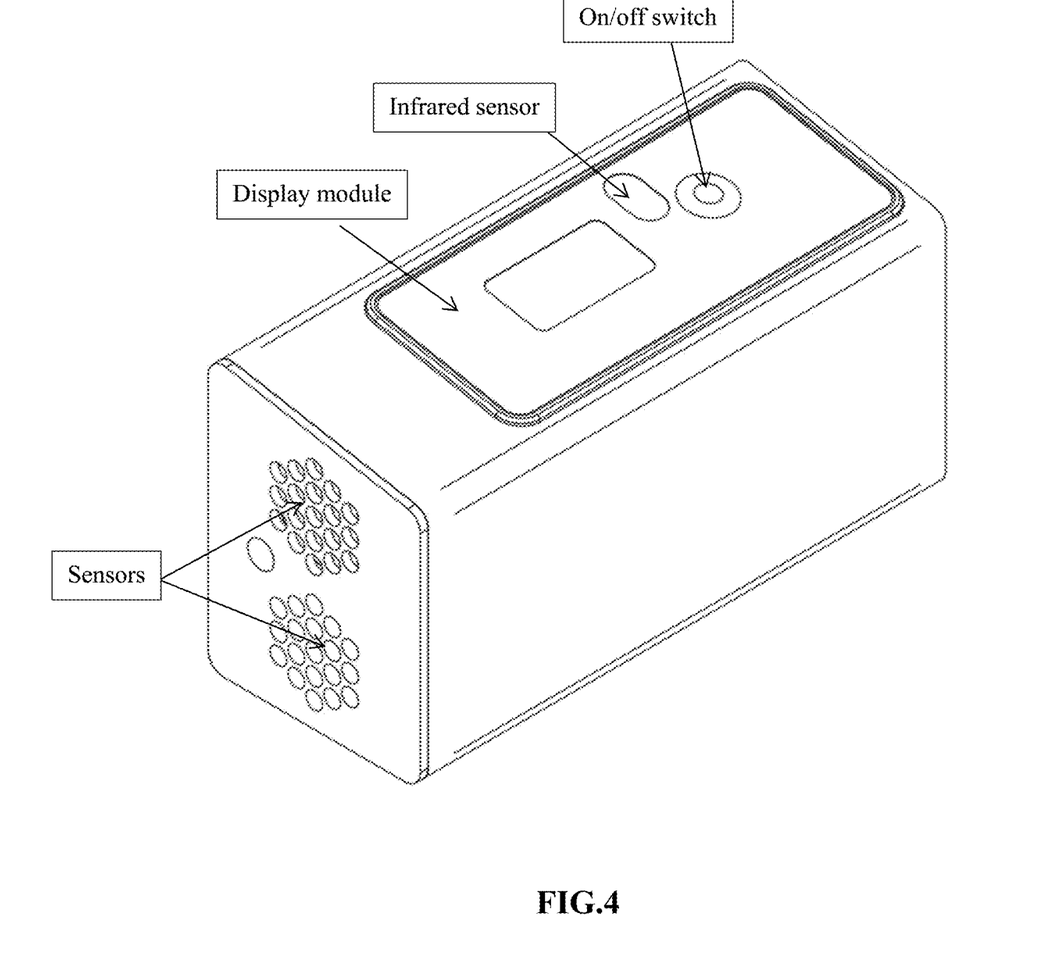
FIG. 4 is an exemplary schematic outside view of the device of FIG. 1.

One exemplary embodiment of a sensor device with a wireless module, a clock, and an infrared sensor for communication with an operator is illustrated in FIG. 2, and FIG. 3 exemplarily depicts another view of the device with display module, on/off switch, and the infrared sensor. With further reference to FIG. 3, the oxygen and carbon dioxide sensors are shown where the actual sensors are disposed in an enclosed volume. Gas exchange with the environment for measurement is facilitated via a gas permeable hydrophobic membrane. In this context, it should be appreciated that use of such membrane provides a significant advantage in that the sensors that would otherwise be readily adversely affected by humidity and/or condensation can be operated in a cell culture container that ordinarily has a relatively high humidity (typically about 95% relative humidity). FIG. 4 exemplarily illustrates an assembled device where the housing has a window through which the display module, the infrared sensor, and the on/off switch are readily accessible, and that has one or more openings through which ambient air can reach the gas permeable membrane.

Figure 5:
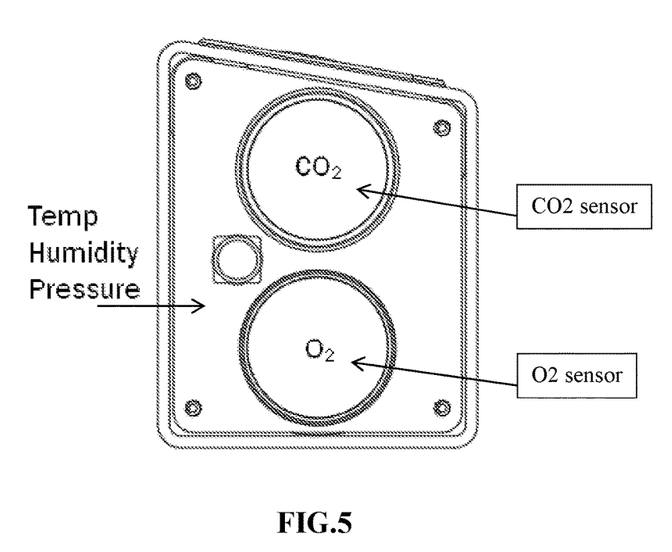
FIG. 5 is an exemplary schematic side view of the device of FIG. 1.

In one embodiment, as illustrated in FIG. 5, the system also comprises a sensor for measuring humidity, a sensor for measuring temperature, a sensor for measuring pressure, and an internal sensor for measuring battery life. These sensors provide data for the compensation for barometric pressure, temperature, and humidity. The electronics and sensors inside the system are preferably encapsulated and sealed from the surrounding environment to prevent deleterious contamination of culturing environment. In one embodiment, the sensors may be positioned at a suitable place to prevent physical damage while allowing fast exchange of gasses. In other embodiments, the display screen is sloped to allow viewing from top and sides without tilting the incubator housing.

Preferred devices are further contemplated to comprise a display screen configured to continuously display information determined by the one or more sensors and/or electronic component. Thus, the display screen may display the amount of oxygen, the amount of carbon dioxide, the temperature, the pressure, humidity, and/or battery life in a continuous manner. If continuous and/or rapid measurements are not desired, the system may go to deep sleep for long term measurements. In those cases, infrared technology using the infrared sensor shown in FIGS. 3 and 4 would wake the device up from low power sleep mode to take periodic measurement. In one example, the display screen may display a variation in color to indicate low battery life. Wireless technologies such as Bluetooth, WIFI, etc. may further be integrated with the system to provide seamless communication between the one or more sensors present in the system and a computer, handheld phone, or other digital device.

In one embodiment, the system may also comprise a real time clock and memory to record and store accurate date and time of measurement. Thus, suitable systems comprises a data storage device that logs and stores the information gathered by the one or more sensors, such as the oxygen sensor and/or the carbon dioxide sensor. The system is adapted to log and store such data for multiple measurements over time. In some embodiments, the system can log data from the one or more sensors every 60 minutes, or more preferably every 45 minutes, or more preferably every 30 minutes, or more preferably every 15 minutes, or more preferably every 1 minute, or more preferably every 30 seconds, or more preferably every 15 seconds, or most preferably every 5 seconds. The data may be stored for a large number of data points, for example between 10-10,000 data points. The data logging and storage unit can log and store data over a long time, for example up to 6 hours, or more preferably up to 12 hours, or more preferably up to 24 hours or more preferably up to 36 hours or more preferably up to 48 hours, or most preferably up to a week. The one or more sensors present in the system would also alert a user if there are any abnormal conditions inside the incubator.

Most typically, the sensor device will be configured to have a flat bottom, which allows for easy placement on perforated surfaces with large gaps. The enclosure of the system is made of non-toxic FDA approved materials, and especially preferred materials include various polymers and aluminum. Therefore, the sensor device may be placed inside a modular incubator chamber (e.g., MIC-101 from BRIncubator) as well as conventional cell culture incubators. Moreover, the sensor device is able to operate in the harsh high-humidity environment of tissue culture incubators. The system comprises solid-state sensors for gas monitoring, eliminating the constant maintenance and re-calibration required by conventional electrochemical and galvanic sensors (for oxygen monitoring) and incandescent IR sensors (for carbon dioxide). It has flexible operating modes, ranging from a rapid data acquisition mode for real-time gas mixing to a low-power mode, waking up on a configurable schedule, allowing for long term data acquisition.

In one embodiment, contemplated devices use industry standard 802.11 WiFi wireless technology for remote monitoring. Multiple units can pair with a separate data aggregator module, which allows remote data logging and instant network access to live as well as logged data via a web browser or by API. In labs without wireless networking, the device can be configured as a direct access point, allowing laptops and mobile devices to connect directly to it.

Figure 6:
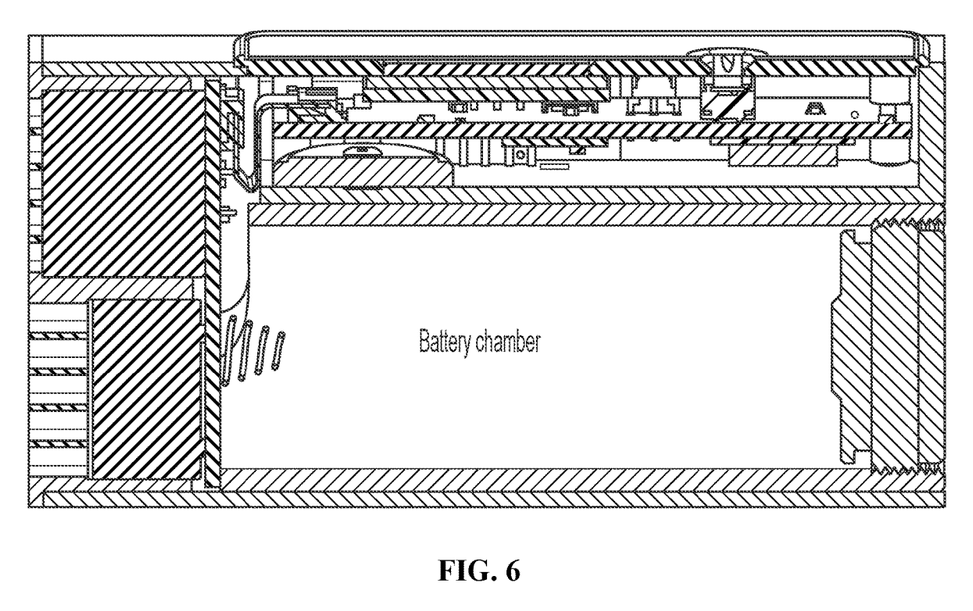
FIG. 6 is an exemplary schematic cross-sectional view of the device of FIG. 1.

The battery used in the system preferably comprises a LiFePO$_4$ battery to support >24 hours in continuous rapid data acquisition mode to over a week at normal data logging rates, and an exemplary battery chamber is illustrated in FIG. 6.

Further disclosed herein is a method for continuously measuring oxygen and carbon dioxide gas levels inside a cell culture incubator, comprising providing a monitor system having an oxygen sensor that uses LED based fluorescence technology to determine the amount of oxygen; a carbon dioxide sensor that uses LED based Non-dispersive Infra-Red (NDIR) technology to determine the amount of carbon dioxide; and electronics to wirelessly monitor the output from the oxygen sensor and carbon dioxide sensor; continuously measuring oxygen and carbon dioxide gas levels inside a cell culture incubator by placing the system inside a cell culture incubator, wherein the sensor readings are pre-compensated for temperature, pressure, and humidity. In one embodiment, this system may be used in tandem to a gas mixing system for measuring oxygen and carbon dioxide.

The oxygen and carbon dioxide monitoring system disclosed herein has a small footprint and fits in compact enclosures. The system does not require re-calibration in normal operation because it is pre-calibrated. The system comprises a safe rechargeable battery technology (LiFePO$_4$) and therefore provides maintenance free use.

There are several advantages of the oxygen and carbon dioxide monitoring system disclosed herein, compared to currently known systems. For example, the instant system provides reliable and accurate performance even in harsh environments; it has a long lifetime and therefore low maintenance; the solid state sensors have no moving parts, non-depleting technology; the system is easy to use, there are virtually no gas cross-sensitivity, works where other sensor technologies don't; it is vibration and shock resistant; compensated for temperature, humidity and pressure; and it is wireless tested to work in water jacketed incubators.

Embodiments of the present disclosure are further described in the following examples. The examples are merely illustrative and do not in any way limit the scope of the invention as claimed.

EXAMPLE 1

Oxygen and Carbon Dioxide Monitor

One embodiment of the oxygen and carbon dioxide monitoring system is disclosed herein, illustrating the description and capabilities of the sensor, the benefits and features. In this embodiment, the system comprises an oxygen sensor, a carbon dioxide sensor, a barometric pressure sensor, a temperature sensor, and a humidity sensor.

The technology for the oxygen sensor comprises solid-state fluorescence quenching and diffusion sampling. The range of the oxygen sensor is 0% to 25% oxygen, the accuracy tolerance is less than 2% FS, and the resolution is 0.1%. The oxygen sensor can operate normally in temperatures ranging from −30° C. to 60° C., and pressure ranging from 500-1200 mbar.

The technology for the carbon dioxide sensor comprises solid-state NDIR with 4.2 um-4.4 um absorption and diffusion sampling. The range of the carbon dioxide sensor is 0% to 20% carbon dioxide with an accuracy tolerance of ±(70 ppm+5% of reading) @STP (standard temperature and pressure). The normal operating conditions of the carbon dioxide sensor is 0° C. to 50° C., but the sensor may have extended operating conditions from −25° C. to 55° C., and a pressure ranging from 500 mbar to 10 bar.

The barometric pressure sensor disclosed in this example has a range between 500 to 1200 mbar, accuracy tolerance of 5 mbar, and resolution of 1 mbar.

The temperature sensor disclosed in this example has a range between −40° C. to 125° C., accuracy tolerance of ±0.2° C. (0° C. to 90° C.), resolution of 0.01° C., and maximum long-term drift of less than 0.03° C. per year.

The humidity sensor in this example has a range between 0% Relative Humidity (RH) to 100% RH, an accuracy tolerance of ±2% RH, resolution of 0.01% RH, hysteresis of ±0.8% RH (@25° C.), and typical long-term drift of less than 0.25% RH/year.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for continuously measuring oxygen and carbon dioxide concentrations inside a cell culture container, comprising:
   providing an environmental sensor device and placing the environmental sensor device into a cell culture container, wherein the sensor device comprises a solid state oxygen sensor and a solid state carbon dioxide sensor;
   establishing a controlled hypoxic atmosphere within the cell culture container, and placing the cell culture container into an incubator;
   using the environmental sensor device to continuously measure oxygen and carbon dioxide concentrations within the cell culture container while the cell culture container is located within the incubator;
   wherein the environmental sensor device measures the oxygen and carbon dioxide concentrations in the cell culture container by passive diffusion of oxygen and carbon dioxide through a gas permeable hydrophobic membrane that separates the solid state oxygen sensor and/or the solid state carbon dioxide sensor from the cell culture container; and
   storing data from the solid state oxygen sensor and the solid state carbon dioxide sensor in a memory and/or wirelessly transmitting the data to a user while the cell culture container is located within the incubator.

2. The method of claim 1, further comprising a step of measuring ambient pressure, humidity, and/or temperature while the cell culture container is located within the incubator.

3. The method of claim 2, further comprising a step of using the measured ambient pressure, humidity, and/or temperature to determine adjusted quantities for the oxygen and carbon dioxide concentrations.

4. The method of claim 3, further comprising a step of displaying the adjusted quantities for the oxygen and carbon dioxide concentrations on a display while the cell culture container is located within the incubator.

5. The method of claim 1, wherein the controlled hypoxic atmosphere in the cell culture container is established using a gas feed into the cell culture container, wherein the gas feed is provided from a gas source outside the incubator.

6. The method of claim 1, wherein the user sends a wireless signal to the environmental sensor device to wirelessly transmit the data to the user.

7. The method of claim 1, wherein the data are stored in predetermined intervals and/or associated with a time stamp.

8. An environmental sensor device, comprising:
   a housing at least partially enclosing first and second solid state sensors;
   wherein the first solid state sensor comprises an oxygen sensor having an oxygen quenchable fluorescent dye;
   wherein the second solid state sensor comprises a non-dispersive infrared (NDIR) carbon dioxide sensor;
   an electronic component that is coupled to the first and second solid state sensors and that comprises a memory for data storage and a wireless communication module that allows for transmission of data while the sensor device is located inside the cell culture incubator;
   wherein the electronic component is configured to compensate sensed amounts of oxygen and carbon dioxide for temperature, pressure, and humidity, to so determine adjusted quantities for oxygen and carbon dioxide; and
   wherein the housing is configured to form a self-contained sensor device suitable for placement inside a cell culture incubator.

9. The device of claim 8, further comprising an ambient pressure sensor, a humidity sensor, and/or a temperature sensor.

10. The device of claim 9, wherein the electronic component is configured to use data from the ambient pressure sensor, the humidity sensor, and/or the temperature sensor to the determine the adjusted quantities for oxygen and carbon dioxide.

11. The device of 10, further comprising a display coupled to the electronic component and configured to display the adjusted quantities for oxygen and carbon dioxide.

12. The method of claim 1, wherein the environmental sensor device is a device according to claim 10.

13. The device of claim 8, further comprising a power source disposed within the housing.

14. The device of claim 13, further comprising a sensor that is coupled to the power source to determine charge status of the power source.

15. The method of claim 1, wherein the environmental sensor device is a device according to claim 8.

* * * * *